US008883465B2

(12) United States Patent
Taden et al.

(10) Patent No.: US 8,883,465 B2
(45) Date of Patent: Nov. 11, 2014

(54) ENZYME-CONTAINING MINI-EMULSIONS

(71) Applicants: Henkel AG & Co. KGAA, Duesseldorf (DE); Max-Planck-Gesellschaft Zur Förderung der Wissenschaften E.V., Munich (DE)

(72) Inventors: Andreas Taden, Duesseldorf (DE); Melanie Hagenbucher, Duesseldorf (DE); Katharina Landfester, Mainz (DE)

(73) Assignees: Henkel AG & Co. KGAA, Duesseldorf (DE); Max-Planck-Gesellschaft zur Forderung der Foerderung der Wissenschaften E.V., Munich (DE)

( * ) Notice: Subject to any disclaimer, the term of this patent is extended or adjusted under 35 U.S.C. 154(b) by 0 days.

(21) Appl. No.: 13/802,862

(22) Filed: Mar. 14, 2013

(65) Prior Publication Data

US 2013/0196395 A1     Aug. 1, 2013

Related U.S. Application Data

(63) Continuation of application No. PCT/EP2011/068874, filed on Oct. 27, 2011.

(30) Foreign Application Priority Data

Oct. 29, 2010   (DE) .......................... 10 2010 049 754

(51) Int. Cl.
    *C12N 9/20*          (2006.01)
(52) U.S. Cl.
    USPC ............................................ 435/136; 435/198
(58) Field of Classification Search
    USPC ................................ 435/18, 136, 198; 264/4
    IPC ...................................... C12P 7/42; C12N 9/20
    See application file for complete search history.

(56) References Cited

U.S. PATENT DOCUMENTS

| | | | |
|---|---|---|---|
| 2008/0020423 A1* | 1/2008 | Groger et al. ................... | 435/41 |
| 2008/0199925 A1 | 8/2008 | Kong et al. | |
| 2008/0275182 A1 | 11/2008 | Kong et al. | |
| 2010/0120617 A1* | 5/2010 | Dyllick-Brenzinger et al. ............................ | 504/100 |

FOREIGN PATENT DOCUMENTS

WO        2004035801 A2      4/2004

OTHER PUBLICATIONS

Fonseca L. P. et al. Biosynthesis and Encapsulation of Aroma Compounds in Miniemulsion. Bioencapsulation International Conference Oct. 1-2, 2010, p. 108.*
Sawaryn C. et al. Benoxazine Miniemulsions Stabilized with Polymerizable Nonionic Benzoxazine Surfactants. Macromolecules 43(21)8933-8941, Nov. 9, 2010.*
Aschenbrenner, Eugen M. et al., "Enzymatic Esterification in Aqueous Miniemulsions" Chemistry: A European Journal, Wiley-VCH Verlag GmbH & Co. KGaA, 2009, 15, pp. 2434-2444.
De Barros, Dragana P.C. et al., "Miniemulsion as Efficient System for Enzymatic Synthesis of Acid Alkyl Esters" Biotechnology and Bioengineering, Wiley Periodicals, Inc., Jul. 1, 2010, vol. 106, No. 4, pp. 507-515.
Wiles, Charlotte et al., "The development and evaluation of a continuous flow process for the lipase-mediated oxidation of alkenes" Beilstein Journal of Organic Chemistry, 2009, 5, No. 27, pp. 1-12.
Crespy, Daniel et al., "Miniemulsion polymerization as a versatile tool for the synthesis of functionalized polymers," Beilstein Journal of Organic Chemistry, 2010, 6, pp. 1132-1148.
Bjoerkling, Fredrik et al., "Lipase Catalyzed Synthesis of Peroxycarboxylic Acids and Lipase Mediated Oxidations." Tetrahedron, Pergamon Press Ltd., 1992, vol. 48, No. 22, pp. 4587-4592.
Xu, Yi et al. "Efficient epoxidation of alkenes with hydrogen peroxide, lactone, and lipase" Green Chem., The Royal Society of Chemistry, 2009, 11, pp. 2047-2051, retrieved from http://pubs.rsc.org on Apr. 5, 2011.
Tufvesson, Paer et al., "Production of glycidyl ethers by chemo-enzymatic epoxidation of allyl ethers" Journal of Molecular Catalysis B: Enzymatic, Elsevier B.V., 54, 2008, vol. 54, pp. 1-6.

* cited by examiner

*Primary Examiner* — Ralph Gitomer
(74) *Attorney, Agent, or Firm* — Sun Hee Lehmann

(57) ABSTRACT

The present invention relates to a mini-emulsion which comprises at least one hydrolase, where the continuous phase of the mini-emulsion contains at least one oxidant, while the dispersed phase comprises at least one $C_{6-60}$ carboxylic acid and optionally at least one reactant. Furthermore, the present invention relates to a method of preparing the mini-emulsion and to a process for the preparation of $C_{6-60}$ percarboxylic acids and to a process for the preparation of an oxidized reactant, in each case using the abovementioned mini-emulsions.

18 Claims, No Drawings

ENZYME-CONTAINING MINI-EMULSIONS

This application is a continuation of PCT/EP2011/068874 filed Oct. 27, 2011 which claims priority to German application 10 2010 049 754.1 filed Oct. 29, 2010.

FIELD OF THE INVENTION

The present invention relates to mini-emulsions which encompass at least one hydrolase. The mini-emulsions according to the invention can be used as a reaction system for preparing various oxidation products, such as for example for preparing $C_{6-60}$ percarboxylic acids, epoxides and/or lactones.

BACKGROUND OF THE INVENTION

As a result of increased requirements for environmental compatibility of chemical reactions, new reactions, production methods and reaction systems with which known or new chemical compounds can be produced in an efficient and environmentally friendly manner are of particular interest.

From ecological points of view, it is particularly important to reduce the energy consumption of chemical reactions and to minimize as far as possible or avoid entirely the use of organic solvents. In many industrial processes today, at least part of the organic solvent is already substituted by water as the reaction medium, provided that the product being prepared does not decompose in or react with water.

Through the use of enzymes, the efficiency of reactions in aqueous reaction media can be increased further. Thus, for example, Landfester et al. describe an effective preparation of carboxylic acid esters in mini-emulsions using lipases (Chem. Eur. J. 2009, 15, 2434-2444), wherein linear $C_{7-12}$ carboxylic acids are reacted with primary alcohols carrying phenyl groups.

Regardless of the state of the art, a need still exists to provide new production methods and/or reaction systems with which known or new chemical compounds can be prepared in an efficient and environmentally friendly manner.

BRIEF SUMMARY OF THE INVENTION

The object of the present invention was therefore to provide new production methods and/or new reaction systems which allow the environmentally friendly and energy-efficient preparation of known or new chemical compounds.

The present object is achieved by the mini-emulsion according to the invention and the methods according to the invention.

The present invention firstly provides a mini-emulsion, encompassing
 a) at least one hydrolase [EC 3.x.x.x],
 b) a continuous phase, containing
  water and
  at least one oxidizing agent and
 c) a dispersed phase, containing
  at least one $C_{6-60}$ carboxylic acid.

DETAILED DESCRIPTION OF THE INVENTION

The term "mini-emulsion" within the meaning of the present invention is understood to mean an emulsion which encompasses a continuous, aqueous phase in which another phase is present in dispersion in the form of drops (dispersed phase), wherein the volume average drop diameter of the dispersed phase is preferably 1 nm to 1000 nm, particularly preferably 30 nm to 800 nm, and most particularly preferably 100 to 600 nm.

The expression "volume average drop diameter" in the context of the present invention always refers to the $D_{50}$ value of the volume average drop diameter, which is determined by means of dynamic light scattering, preferably using a NICOMP 380 submicron particle sizer from PSS NICOMP, USA. With the use of a NICOMP 380 submicron particle sizer, the corresponding measurement is performed at a temperature of 23° C. using a laser with a wavelength of 635 nm at a scattering angle of 90°, the mini-emulsion according to the invention being diluted using deionized water before performing the measurement, to the extent that no concentration effects or multiple scatterings occur.

The volume average drop diameter ($D_{50}$) here is the value of the integral volume distribution at which 50 vol. % of the dispersed phase has a smaller diameter than the diameter that corresponds to the $D_{50}$ value.

The mini-emulsion of the present invention can be prepared by the input of high shear forces, for example using ultrasound, and is generally kinetically stable. The stability can additionally be increased by adding one or more surface-active substance(s) and/or hydrophobic substance(s) to the mini-emulsion according to the invention.

With the aid of the mini-emulsion of the present invention it is possible to oxidize a $C_{6-60}$ carboxylic acid in a low-impact and efficient method to form the corresponding $C_{6-60}$ percarboxylic acid.

The present invention therefore also provides a method for preparing $C_{6-60}$ percarboxylic acids by exposing the mini-emulsion according to the invention to a temperature of 5° to 95° C. for at least one minute.

In a particularly preferred embodiment of the invention, the dispersed phase of the mini-emulsion according to the invention additionally encompasses at least one reactant.

A reactant within the meaning of the present invention is understood to mean a compound which can be reacted with a $C_{6-60}$ percarboxylic acid so that preferably at least 5 mole %, particularly preferably at least 10 mole %, and most particularly preferably at least 20 mole %, of all of the molecules of the reactant have a different chemical structure after 10 hours compared with before the reaction.

A reactant, i.e. a compound which can be reacted with a $C_{6-60}$ percarboxylic acid, is preferably understood within the meaning of the present invention to be a compound which is distinguished by the fact that, in the reaction of a 1 molar solution of said compound in chloroform at 30° C. with an equimolar quantity of $C_{6-60}$ percarboxylic acids, at least 5 mole %, particularly preferably at least 10 mole %, and most particularly preferably at least 20 mole %, of all of the molecules of the reactant have a different chemical structure after 10 hours compared with before the reaction.

A mini-emulsion of the present invention, of which the dispersed phase additionally comprises at least one reactant, can be used in particular for the selective, energy-efficient and environmentally friendly preparation of oxidation products of one or more of the reactants employed.

The present invention therefore also provides a method for preparing an oxidation product of a reactant, encompassing the following steps:
 a) preparation of a mini-emulsion according to the invention;
 b) addition of at least one reactant for preparing a mini-emulsion according to the invention, the dispersed phase of which additionally contains at least one reactant;

c) oxidation of the reactant by exposing the mini-emulsion from step b) to a temperature of 5° to 95° C. for at least one minute.

Suitable reactants are, for example, alkenes and/or cyclic ketones, which can be converted selectively to epoxides and/or lactones by the method described above. The mini-emulsion of the present invention, the dispersed phase of which additionally contains at least one reactant, is thus a suitable reaction system for the selective, energy-efficient and environmentally friendly preparation of oxidation products of one or more reactants, wherein the said reaction system can be used in particular for preparing epoxides and/or lactones.

The present invention additionally provides a method for preparing the mini-emulsion according to the invention, encompassing the following steps:

i) preparing a mixture encompassing water, at least one oxidizing agent, at least one $C_{6-60}$ carboxylic acid and optionally at least one reactant, ii) production of a mini-emulsion by input of shear forces and iii) addition of at least one hydrolase [EC 3.x.x.x].

In order to provide additional stabilizing of the mini-emulsion, the mini-emulsion of the present invention can preferably contain at least one further component which is selected from surfactants or hydrophobic substances (hydrophobes). In particular, it is advantageous for the mini-emulsion according to the invention to contain at least one hydrophobic substance (hydrophobe) and at least one surfactant. The mini-emulsion according to the invention can, of course, also contain mixtures of various hydrophobic substances and/or mixtures of various surfactants.

Hydrophobic substances or hydrophobes have extremely low water solubility and are therefore generally a component of the dispersed phase. As a result of the hydrophobes, mass exchange between the various droplets of the dispersed phase is inhibited or suppressed and thus the undesirable Ostwald ripening of the drops of the dispersed phase, which leads to a growth of the drop size, is reduced or completely prevented.

Preferred hydrophobic substances (hydrophobes) within the meaning of the present invention are selected from hydrocarbons containing 10 to 100 C atoms, preferably 10 to 40 C atoms. Suitable hydrophobes are, for example, hexadecane, octadecane, eicosane, pentacosane, cetyl alcohol, stearyl alcohol, octacosan-1-ol, myristyl alcohol, 2-methylhexadecan-1-ol, long-chain oils, such as for instance plant oils, e.g. olive oil, fatty acid alkyl esters, halogenated hydrocarbons, e.g. fluorinated hydrocarbons, silanes, organosilanes, siloxanes, capped isocyanates, alkyl methacrylate, pentaerythritol triacrylate or trimethacrylate, and hydrophobic oligomeric polymerization, polycondensation and/or polyaddition products.

Preferably, the content of hydrophobic substance (hydrophobe) in the mini-emulsion according to the invention is 0.05 to 7.5 wt. %, preferably 0.1 to 5 wt. %, and in particular 0.1 to 1.5 wt. %, based in each case on the total quantity of the mini-emulsion.

As well as an additional stabilizing of the mini-emulsion according to the invention, the droplet size of the dispersed phase can be readily adjusted in the ranges stated by means of the type and concentration of surfactants used. As surfactants, as well as ionic surfactants, such as for example anionic or cationic surfactants, in particular nonionic surfactants can be used, since these have only a slight influence on the activity of the hydrolase used.

Examples of suitable cationic surfactants according to the invention are those compounds which are selected in particular from quaternary ammonium compounds, such as dimethyl distearyl ammonium chloride, Stepantex VL 90 (Stepan), hexadecyl trimethyl ammonium chloride, Dehyquart A (cetrimonium chloride or CTMA-Cl, BASF SE) or Dehyquart LDB 50 (lauryl dimethyl benzyl ammonium chloride; BASF SE), ester quats, in particular quaternized fatty acid trialkanolamine ester salts and/or salts of long-chain primary amines of quaternary ammonium compounds.

Examples of suitable anionic surfactants according to the invention are those compounds which are selected in particular from soaps, alkylbenzenesulfonates, alkane sulfonates, olefin sulfonates, alkyl ether sulfonates, glycerol ether sulfonates, α-methyl ester sulfonates, sulfo fatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfo triglycerides, amide soaps, ether carboxylic acids and salts thereof; fatty acid isothionates, fatty acid sarcosinates, fatty acid taurides, N-acyl amino acids such as acyl lactylates, acyl tartrates, acyl glutamates and acyl aspartates, alkyl oligoglucoside sulfates, protein fatty acid condensates, in particular plant products based on wheat, and/or alkyl (ether) phosphates.

According to the invention, both low molecular weight and polymeric nonionic surfactants can be used as nonionic surfactants. Suitable nonionic surfactants are selected in particular from low molecular weight, non-polymeric, nonionic surfactants, such as alkoxylated, preferably ethoxylated, fatty alcohols, alkyl phenols, fatty amines and fatty acid amides; alkoxylated triglycerides, mixed ethers and mixed formals; optionally partially oxidized alk(en)yl oligoglycosides, glucoronic acid derivatives, fatty acid N-alkyl glucamides, protein hydrolyzates, sugar esters, sorbitan esters and/or amine oxides. Furthermore, the nonionic surfactants can be selected from polymeric nonionic surfactants, such as fatty alcohol polyglycol ethers, alkylphenol polyglycol ethers, fatty acid polyglycol esters, fatty acid amide polyglycol ethers, fatty amine polyglycol ethers, polyol fatty acid esters and/or polysorbates.

In particular, it is advantageous to use a nonionic surfactant as surfactant, with ethoxylated fatty alcohols, such as for example Lutensol AT50, Lutensol AT 25, Lutensol AT 80 from BASF SE, and ethylated lauryl alcohols, myristyl alcohols, cetyl alcohols, stearyl alcohols, arachidyl alcohols, behenyl alcohols, oleyl alcohols, elaidyl alcohols, gadoleyl alcohols, arachidonyl alcohols, erucyl alcohols and/or brassidyl alcohols being preferred.

It is also possible to use any mixtures of the aforementioned surfactants.

Preferably, the content of surfactant in the mini-emulsion according to the invention is 0.01 to 15 wt. %, preferably 0.05 to 10 wt. %, and in particular 0.1 to 5 wt. %, based in each case on the total quantity of the mini-emulsion.

The mini-emulsion according to the invention must comprise at least one hydrolase or a mixture of various hydrolases. A hydrolase is to be understood in particular as those enzymes that are allocated to the EC class 3.x.x.x. The hydrolase has the effect that the conversion reaction taking place in the mini-emulsion according to the invention is accelerated and its energy requirement reduced, so that the mini-emulsion according to the invention can be used effectively as a reaction system for preparing $C_{6-60}$ percarboxylic acids or, in the event that the disperse phase additionally encompasses at least one reactant, for preparing the corresponding oxidation products of the reactants, such as for example epoxides and/or lactones.

The hydrolase is preferably selected from esterases [EC 3.1.x.x] and in particular from carboxylic ester hydrolases [EC 3.1.1.x], since these permit a particularly effective conversion reaction in the mini-emulsion according to the invention. The efficiency of the conversion reaction can be further increased if a lipase [EC 3.1.1.3] is used as hydrolase, the lipase particularly preferably being selected from naturally existing lipases.

Naturally existing in this context means that the lipase is a lipase which is inherent to the microorganism. It is therefore a lipase of the microorganism, which expresses this in its wild-type form and/or for which the genetic information is present in its genome without any genetic engineering modification. Naturally existing lipases are therefore in particular not to be understood as those lipases which have been introduced into a microorganism with the aid of a genetic engineering method and expressed by this in recombinant fashion.

Within the framework of the present invention, naturally existing lipases can preferably be selected from: lipase from *Thermomyces lanuginosus*, lipase PS from *Pseudomonas cepacia*, lipase PS from *Pseudomonas stutzeri*, lipase RS from *Rhizopus* sp., lipase PF from *Pseudomonas fluorescens*, lipase PC from *Penicillium camenbertii*, lipase P1 from *Pseudomonas cepacia*, lipase AN from *Aspergillus niger*, lipase A from *Achromobacter* sp., lipase AS1 from *Alcaligenes* sp., lipase AS2 *Alcaligenes* sp., lipase C2 from *Candida cylindracea*, lipase C from *Candida cylindracea*, lipase lipozyme TL IM, lipase lipozyme TL 100L, *Candida antarctica* lipase B (CALB), *Candida antarctica* lipase A (CALA) and *Candida rugosa* lipase (CRL).

Mixtures of the aforementioned lipases can also be used.

Lipase PS from *Pseudomonas cepacia* and *Candida antarctica* lipase B (CALB) are most particularly preferred here, since, in the event of the presence of a reactant in the mini-emulsion according to the invention, these permit a particularly effective preparation of the oxidation product of the respective reactant. Thus, for example, epoxides can be prepared from alkenes (as reactants) in high yields with the aid of the aforementioned lipases, only a small quantity of diol being obtained as an undesirable secondary product of oxidation.

To increase the reusability of the hydrolase of the present invention, this can be immobilized on a suitable support material. Suitable support materials here can be selected in particular from polymeric materials, such as for instance poly(meth)acrylates, crosslinkable resin prepolymers, membranes, polyamides, polyethylene glycols, polypropylene glycols, polyurethanes, polyvinyl chlorides, silicones, sol-gel products and/or phyllosilicates. Other suitable support materials are, for example, acrylic material, alginate, celite, cellulose, duolite, decyl chloroacetate emulsions, silanized glasses, glass wool and/or kieselguhr.

A suitable commercially available immobilized lipase is, for example, *Candida antarctica* lipase B (CALB) immobilized on acrylic resin, which is marketed by Novozymes with the trade name Novozym 435, and the lipases *Candida antarctica* lipase A (CALA) and *Candida Rugosa* lipase (CRL) likewise immobilized on acrylic resin, which are each marketed by Chiral Vision with the trade name Immozymes.

In the event that the hydrolase is applied onto a support material, the quantitative proportions of the hydrolase or lipase given below refer to the total quantity of enzyme and support material.

Preferably, the content of hydrolase in the mini-emulsion according to the invention is 0.01 to 5 wt. %, particularly preferably 0.03 to 3 wt. %, and in particular 0.05 to 1.5 wt. %, based in each case on the total quantity of the mini-emulsion.

In the event that the mini-emulsion according to the invention encompasses at least one reactant, it is in particular advantageous for the proportion of the hydrolase, based on the total quantity of reactant, to be 0.5 to 20 wt. %, preferably 0.75 to 15 wt. %, particularly preferably 1 to 9 wt. %, and most preferably 2 to 7.5 wt. %.

If the mini-emulsion according to the invention contains at least one alkene as reactant, it is in particular advantageous for the hydrolase to be selected from lipases and the proportion of the lipase, based on the total quantity of alkene, to be 0.5 to 20 wt. %, preferably 0.75 to 15 wt. %, particularly preferably 1 to 9 wt. %, and most preferably 2 to 7.5 wt. %.

In the above quantitative ranges, a particularly efficient conversion of the alkene to the epoxide as the corresponding oxidation product is possible, with only small quantities of undesirable secondary products of oxidation, such as for example diols, being obtained.

The continuous phase of the mini-emulsion according to the invention contains water. In addition to water, the said phase can also encompass organic solvents, with those organic solvents which are miscible with water under the conditions stated being particularly suitable. Suitable organic solvents are, for example, primary alcohols, such as for instance ethanol, n-propanol, isopropanol, n-butanol, isobutanol and ethers, such as for instance tetrahydrofuran, and/or any mixtures thereof.

In particular, however, within the meaning of the present invention it is advantageous for the continuous phase or the entire mini-emulsion according to the invention to be substantially free from organic solvents.

A continuous phase which is substantially free from organic solvents within the meaning of the present invention means that the proportion of all organic solvents in the total quantity of the continuous phase is less than 1 wt. %, preferably less than 0.1 wt. %, particularly preferably less than 0.01 wt. %, and most preferably less than 0.001 wt. %.

A mini-emulsion which is substantially free from organic solvents within the meaning of the present invention means that the proportion of all organic solvents in the total quantity of the mini-emulsion according to the invention is less than 1 wt. %, preferably less than 0.1 wt. %, particularly preferably less than 0.01 wt. %, and most preferably less than 0.001 wt. %.

In a particularly preferred embodiment, the continuous phase of the mini-emulsion according to the invention or the mini-emulsion according to the invention is completely free from organic solvents.

The continuous phase of the mini-emulsion according to the invention further encompasses at least one oxidizing agent or a mixture of various oxidizing agents. An oxidizing agent within the meaning of the present invention is understood to be a compound with the aid of which a $C_{6-60}$ carboxylic acid can be converted or oxidized in the presence of a hydrolase to form the corresponding $C_{6-60}$ percarboxylic acid.

Although the oxidizing agent is a component of the continuous phase, part of the oxidizing agent can also be present in dissolved and/or dispersed form in the dispersed phase. However, in terms of reaction efficiency it is advantageous if at least 90 wt. %, preferably at least 95 wt. %, particularly preferably at least 99 wt. %, and most preferably at least 99.5 wt. %, of the total quantity of the oxidizing agent is a component of the continuous phase.

The oxidizing agent is preferably selected from peroxide compounds. In a preferred embodiment of the invention, the oxidizing agent is selected from hydrogen peroxide and/or hydrogen peroxide-releasing reagents.

The term "hydrogen peroxide-releasing reagents" within the meaning of the present invention is understood to mean compounds which release hydrogen peroxide under the conditions given, for example in a decomposition reaction and/or a decomplexation reaction. Examples of hydrogen peroxide-releasing reagents include perborates, in particular sodium perborate, percarbonates, in particular sodium percarbonate, persulfates and/or amine-hydrogen peroxide complexes.

As oxidizing agents within the meaning of the present invention, amine-hydrogen peroxide complexes are particularly suitable owing to their safe handling properties. In addition, amine-hydrogen peroxide complexes are able to release hydrogen peroxide under mild conditions.

As amine in the amine-hydrogen peroxide complexes of the present invention, in particular those compounds having at least one functional group of the following formula

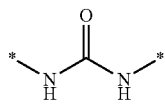

are preferred.

A most particularly preferred oxidizing agent within the meaning of the present invention is hydrogen peroxide-urea [CAS 124-43-6], an amine-hydrogen peroxide complex which is also marketed with the names carbamide peroxide, percarbamide or UHP.

Preferably, the content of oxidizing agent in the mini-emulsion according to the invention is 10 to 50 wt. %, preferably 13.5 to 30 wt. %, and most preferably 15 to 25 wt. %, based in each case on the total quantity of the mini-emulsion.

In the event that the mini-emulsion according to the invention encompasses at least one reactant, it is particularly advantageous for the molar ratio of oxidizing agent to reactant to be 1:1 to 3:1, preferably 1.1:1 to 2.5:1, particularly preferably 1.2:1 to 2:1, and most particularly preferably 1.25:1 to 1.75:1.

In the event that the mini-emulsion according to the invention encompasses at least one reactant, it is furthermore advantageous for the proportion of the oxidizing agent, based on the total quantity of the mini-emulsion according to the invention, to be 10 to 50 wt. %, preferably 13.5 to 30 wt. % wt. %, and most preferably 15 to 20 wt. %.

In the event that the mini-emulsion according to the invention encompasses at least one alkene as reactant, it is moreover advantageous for the proportion of the oxidizing agent, based on the total quantity of the mini-emulsion according to the invention, to be 10 to 50 wt. %, preferably 13.5 to 30 wt. %, and most preferably 15 to 20 wt. %, and/or for the molar ratio of oxidizing agent to reactant to be 1:1 to 3:1, preferably 1.1:1 to 2.5:1, particularly preferably 1.2:1 to 2:1, and most particularly preferably 1.25:1 to 1.75:1.

The pH value of the continuous phase is preferably between 3.5 and 10 and most preferably between 4 and 7, since in the said pH ranges the activity of the hydrolase, such as for example the lipase, is highest and undesirable secondary reactions are minimized.

The dispersed phase of the mini-emulsion according to the invention contains at least one $C_{6-60}$ carboxylic acid or a mixture of various $C_{6-60}$ carboxylic acids.

Although the $C_{6-60}$ carboxylic acid is a component of the dispersed phase, part of the $C_{6-60}$ carboxylic acid can also be present in dissolved and/or dispersed form in the continuous phase. However, it is particularly advantageous within the meaning of the present invention if at least 90 wt. %, preferably at least 95 wt. %, particularly preferably at least 99 wt. %, and most preferably at least 99.5 wt. %, of the total quantity of the $C_{6-60}$ carboxylic acid is a component of the dispersed phase.

The $C_{6-60}$ carboxylic acid of the present invention can encompass one or more carboxylic acid groups, $C_{6-60}$ carboxylic acids which encompass only one carboxylic acid group being preferred within the meaning of the present invention, these therefore being $C_{6-60}$ monocarboxylic acids.

The $C_{6-60}$ carboxylic acid of the present invention can have a linear or branched structure, linear $C_{6-60}$ carboxylic acids being preferred. In addition, the $C_{6-60}$ carboxylic acid can have one or more substituents, suitable substituents being selected, for example, from halogen, nitro, cyano, hydroxyl and/or amino.

Suitable as $C_{6-60}$ carboxylic acid are in particular those carboxylic acids that contain 7, 8, 9, 10, 11, 12, 13, 14, 15 or 16 C atoms, particularly high reaction conversions being obtained if $C_{6-60}$ carboxylic acids which encompass 7, 8, 9, 10, 11 or 12 C atoms are used in the mini-emulsion according to the invention. It is particularly advantageous if the $C_{6-60}$ carboxylic acid of the present invention is selected from linear $C_{7-12}$ carboxylic acids, such as e.g. heptanoic acid, octanoic acid, nonanoic acid, decanoic acid, undecanoic acid or dodecanoic acid and/or from any mixtures thereof, since in this way particularly high reaction conversions can be achieved.

In certain embodiments, the content of $C_{6-60}$ carboxylic acid in the mini-emulsion according to the invention is 0.05 to 10 wt. %, preferably 0.1 to 5 wt. %, and most preferably 0.2 to 3 wt. %, based in each case on the total quantity of the mini-emulsion.

In the event that the mini-emulsion according to the invention encompasses at least one reactant, it is particularly advantageous for the content of $C_{6-60}$ carboxylic acid in the mini-emulsion according to the invention to be 0.05 to 15 mole %, preferably 0.1 to 10 mole %, and most preferably 2.5 to 7.5 mole %, based in each case on the total quantity of reactant.

In the event that the mini-emulsion according to the invention encompasses at least one reactant, it is furthermore advantageous for the molar ratio of $C_{6-60}$ carboxylic acid to reactant to be 10:1 to 1:10,000, preferably 1:1 to 1:5000, particularly preferably 1:10 to 1:2500, and most particularly preferably 1:10 to 1:100.

In the event that the mini-emulsion according to the invention encompasses at least one alkene as reactant, it is moreover advantageous for the proportion of the $C_{6-60}$ carboxylic acid, based on the total quantity of the mini-emulsion according to the invention, to be 0.05 to 10 wt. %, preferably 0.1 to 5 wt. %, and particularly preferably 0.2 to 3 wt. %, and/or for the molar ratio of $C_{6-60}$ carboxylic acid to reactant to be 10:1 to 1:10,000, preferably 1:1 to 1:5000, particularly preferably 1:10 to 1:2500, and most particularly preferably 1:10 to 1:100.

A mini-emulsion according to the invention, the dispersed phase of which additionally encompasses at least one reactant, is an effective reaction system which can be used for preparing oxidation products of the respective reactants. In particular, the aforementioned mini-emulsion is suitable for preparing epoxides and/or lactones which can be obtained starting from alkenes and/or cyclic ketones.

Through the use of the mini-emulsion according to the invention, in comparison to conventional emulsions, such as for example macro-emulsions, substantially higher reaction conversions can be achieved with significantly lower quantities of surfactants being needed to stabilize the emulsion. Through the use of the mini-emulsion according to the invention, the quantity of undesirably occurring by-products can furthermore be reduced. Thus, for example, it is possible to reduce the quantity of diol as an undesirable by-product in the preparation of epoxides by oxidation of alkenes by using a mini-emulsion of the present invention instead of a conventional macro-emulsion.

Although the reactant of the present invention is generally a component of the dispersed phase, part of the reactant can also be present in dissolved and/or dispersed form in the continuous phase. However, in terms of the reaction efficiency of the present invention it is advantageous if at least 90 wt. %, preferably at least 95 wt. %, particularly preferably at least 99 wt. %, and most preferably at least 99.9 wt. %, of the total quantity of the reactant is a component of the dispersed phase. To prevent larger quantities of the reactant from being present in dissolved and/or dispersed form in the continuous, aqueous phase, in particular substances having low solubility in water are used as reactants within the meaning of the present compound.

Within the meaning of the present invention, "substances having low solubility in water" are understood to be in particular those compounds of which the solubility in water (pH=7.0) at 22° C. and 1013 mbar is less than 0.2 mol/l, particularly preferably less than 0.1 mol/l and most preferably less than 0.01 mol/l.

For preparing epoxides, in particular alkenes are suitable as reactants. Alkenes within the meaning of the present invention are understood to be all compounds having at least one C—C double bond. The alkene can also encompass more than one double bond, such as e.g. in dienes or trienes. Suitable alkenes are, for example, compounds which contain at least one terminal and/or at least one internal C—C double bond, it being possible for the alkene to have either a cyclic or an acyclic structure. High yields are obtained in preparing epoxides in particular if the alkene as reactant encompasses 5 to 40 C atoms, preferably 6 to 20 C atoms. The alkene can be a hydrocarbon (i.e. containing only carbon and hydrogen atoms) or can also encompass at least one functional group, such as e.g. halide, carboxyl, hydroxyl, ether, carbonyl, cyano or nitro residues.

Examples of acyclic alkenes are mono- or polyunsaturated alkenes with 6 to 20 C atoms, such as e.g. aromatic vinyl compounds, unsaturated fatty acids or linear alkenes with terminal or internal C—C double bonds.

Examples of cyclic alkenes are mono- or polyunsaturated alkenes with 6 to 20 C atoms in the ring. Particularly preferred are in particular cyclohexene, cycloheptene, cyclooctene, cyclooctadiene, cyclododecene, cyclododecadiene, cyclododecatriene, dicyclopentadiene and/or cyclododecene.

For preparing lactones, in particular cyclic ketones are suitable as reactants, which are oxidized with the aid of the mini-emulsion according to the invention as reaction system in a Bayer-Villiger reaction to form the corresponding lactones. Suitable cyclic ketones here preferably encompass 5 to 12 C atoms in the ring. The cyclic ketone here can encompass one or more substituents, which are preferably selected from halide, carboxyl, hydroxyl, ether, carbonyl, cyano or nitro residues.

Examples of cyclic ketones include cyclopentanone, cyclohexanone, cycloheptanone and/or cyclooctanone.

Further reactants which can be converted to the corresponding oxidation products with the aid of the mini-emulsion according to the invention are, for example:
  secondary amines, which are oxidized to form disubstituted hydroxylamines;
  aromatics, in particular polynuclear aromatics, such as naphthalene, alkyl naphthalenes, anthracenes and/or alkyl anthracenes, which are converted to the corresponding quinone bodies;
  organic sulfides, which are converted to the sulfoxides or sulfones; and
  aromatic amines, which are converted to nitroso amines, and aromatic N,N-dialkylamines, which are converted to the corresponding N-oxides.

The present invention further provides a method for preparing an oxidation product of a reactant, encompassing the following steps:
  a) preparation of a mini-emulsion according to the invention;
  b) addition of at least one reactant for preparing a mini-emulsion according to the invention, the dispersed phase of which additionally contains at least one reactant;
  c) oxidation of the reactant by exposing the mini-emulsion from step b) to a temperature of 5° C. to 95° C. for at least one minute.

In the method according to the invention for preparing an oxidation product of a reactant, all embodiments of the mini-emulsion described in connection with the mini-emulsion according to the invention can be used.

In step c) of the method according to the invention, the oxidation of at least one reactant preferably takes place by exposing the mini-emulsion to a temperature of 5° C. to 95° C., for example with stirring or shaking, for 10 minutes to 150 hours, particularly preferably for 30 minutes to 120 hours, most particularly preferably for 1 hour to 100 hours, and most preferably for 20 hours to 80 hours.

In particular in step c) of the method according to the invention, the oxidation of at least one reactant takes place by exposing the mini-emulsion to a temperature of preferably 10° C. to 95° C., particularly preferably of 20° C. to 80° C. and most particularly preferably of 30° C. to 60° C. for at least one minute.

For example in the method according to the invention the oxidation of at least one reactant takes place by exposing the mini-emulsion according to the invention to a temperature of 10° C. to 95° C. for 10 minutes to 150 hours, or to a temperature of 20° C. to 80° C. for 30 minutes to 120 hours, or to a temperature of 30° C. to 60° C. for 20 hours to 80 hours.

In principle, the method according to the invention for preparing an oxidation product of a reactant can be carried out continuously or batchwise. If the method is performed batchwise, the procedure is preferably that, during step c) of the method according to the invention, the mini-emulsion as reaction system is shaken and/or stirred in a reaction vessel or reaction reactor. The reaction vessel in this case can be heated or cooled from the outside or the inside in at least one section.

In an alternative embodiment, the method according to the invention for preparing an oxidation product of a reactant is carried out continuously in a flow reactor, which can be at least partially filled with a heating medium or heated from outside by suitable means. The mini-emulsion according to the invention in this case flows continuously through the flow reactor, at least in step c) of the method according to the invention.

The term "continuously" here is understood in the conventional manner as a way of operating in which the mini-emulsion flows through the reactor at least over a period such that a total volume of a mini-emulsion which is large in comparison with the internal volume of the reactor itself has flowed through the reactor before the flow of the mini-emulsion is interrupted. "Large" in this sense means: "at least twice as large". Naturally, a continuous reaction of this type also has a beginning and an end.

The present invention also provides a method for preparing a mini-emulsion according to the invention, encompassing the following steps:

i) preparing a mixture encompassing water, at least one oxidizing agent, which is preferably selected from hydrogen peroxide and/or hydrogen peroxide-releasing reagents, at least one $C_{6-60}$ carboxylic acid and optionally at least one reactant, ii) production of a mini-emulsion by the input of shear forces and iii) addition of at least one hydrolase [EC 3.x.x.x].

In the method according to the invention for preparing the mini-emulsion, all oxidizing agents, $C_{6-60}$ carboxylic acids, reactants and hydrolases described in connection with the mini-emulsion according to the invention can be used.

In step i), a mixture which encompasses water, at least one oxidizing agent, at least one $C_{6-60}$ carboxylic acid and optionally at least one reactant is prepared by blending. The mixture is in particular a macro-emulsion. Then, in step ii) of the method according to the invention, a mini-emulsion is produced by the input of shear forces. The fine distribution of the disperse phase, and thus the formation of the mini-emulsion, is generally achieved by a high local energy input, such as for example by the treatment of the mixture from step i) using ultrasound, by high-pressure homogenization and/or by a micro-fluidizer. For preparing the mini-emulsion in step ii) of the method according to the invention, for example a macro-emulsion produced in step i) can be exposed to an ultrasound treatment at 10-60 kHz for a period of e.g. less than 300 seconds. In general, it applies that the droplet size of the dispersed phase can be controlled by the use of hydrophobic substances (hydrophobes) and/or surfactants, and by the quantity of energy input, e.g. by the choice of a suitable homogenizing pressure or by the adjustment of an appropriate ultrasound energy.

Then, in step iii) of the method according to the invention, at least one hydrolase (EC-class 3.x.x.x) or a mixture of various hydrolases is added, optionally and shaking and/or stirring. In this way, a mini-emulsion of the present invention is produced, which can be used as a reaction system for preparing $C_{6-60}$ percarboxylic acids or, in the event of the presence of a suitable reactant, for preparing oxidation products of the respective reactant.

EXAMPLES

A) General Specification for Preparing a Mini-Emulsion According to the Invention A solution of reactant (alkene), carboxylic acid and hydrophobe was added to a surfactant-containing aqueous solution, to which an oxidizing agent had been added. The resulting two-phase system was pre-homogenized for 1 hour with stirring. The macro-emulsion was then subjected using a "½" ultrasound probe (amplitude 90%) to a total ultrasound time of 2 minutes. To the resulting mini-emulsion a lipase was then added and the resulting mixture was then reacted at the temperature stated in a shaker (at 400 rpm).

B) Preparation of Various Oxidation Products of Alkenes

A mini-emulsion, which contains the components stated in the quantities stated, was exposed to the said conditions, so that substantially the corresponding epoxides are obtained as oxidation product of the alkenes used, with diols being formed as undesirable secondary products of oxidation. UHP, i.e. percarbamide [CAS 124-43-6], was used as oxidizing agent.

To determine the reaction conversions, the product mixture was extracted from the emulsion using chloroform on completion of the reaction. From the product mixture, which substantially contained unreacted olefin, epoxide and diol, the reaction conversion stated was determined by gas chromatography (GC).

| Alkene | Time [h] | Epoxide conversion [%] | Diol conversion [%] | Reaction conditions |
|---|---|---|---|---|
| Styrene | 48 | 75.3 | 6.0 | 2.5 g styrene, 10 mole % decanoic acid, 1.5 eq. UHP, 5 wt. % lipase (all based on alkene); 12.5 ml water, 0.5 wt. % surfactant LUTENSOL AT50 (based on water); temperature 40° C.; pH value at start of reaction = 7 |
| 1-Phenyl-cyclohexene | 51 | 96.2 | 3.8 | 2.5 g styrene, 10 mole % decanoic acid, 1.5 eq. UHP, 5 wt. % lipase (all based on alkene); 12.5 ml water, 0.5 wt. % surfactant LUTENSOL AT50 (based on water); temperature 40° C.; pH value at start of reaction = 7 |
| Cyclooctene | 11 | 100.0 | — | 2.5 g styrene, 10 mole % decanoic acid, 1.5 eq. UHP, 5 wt. % lipase (all based on alkene); 12.5 ml water, 2.0 wt. % LUTENSOL AT50 (based on water); temperature 40° C.; pH value at start of reaction = 4.2 |
| 1-Octene | 64 | 26.0 | — | 2.5 g styrene, 10 mole % decanoic acid, 1.5 eq. UHP, 5 wt. % lipase (all based on alkene); 12.5 ml water, 2.0 wt. % surfactant LUTENSOL AT50 (based on water); |

| Alkene | Time [h] | Epoxide conversion [%] | Diol conversion [%] | Reaction conditions |
|---|---|---|---|---|
| Oleic acid | 24 | 94.7 | — | temperature 40° C.; pH value at start of reaction = 4.2 2.5 g styrene, 10 mole % decanoic acid, 1.5 eq. UHP, 5 wt. % lipase (all based on alkene); 12.5 ml water, 2.0 wt. % surfactant LUTENSOL AT50 (based on water); temperature 40° C.; pH value at start of reaction = 4.2 |

The above table shows that, with the aid of the mini-emulsion according to the invention, a wide substrate variety of alkenes can be converted to the corresponding oxidation products (epoxides).

C) Preparation of Styrene Oxides Using Various Enzyme Concentrations

Mini-emulsions were prepared, which contained the following components: 2.5 g styrene, 10 mole % decanoic acid, 1.5 eq. UHP (all based on alkene); 12.5 ml water, 2.0 wt.% surfactant LUTENSOL AT50 (based on water); temperature 40° C.; pH value at start of reaction=4.2; and various quantities of lipase PS.

With a lipase content of 5 wt. %, a volume average drop diameter ($D_{50}$) of the disperse phase of 222 nm, measured by dynamic light scattering using a NICOMP 380 submicron particle sizer from PSS NICOMP, USA, was determined. The reaction conversion was determined as above.

| Quantity of lipase PS based on styrene [eq.] | Time (max. epoxide conversion) [h] | Epoxide conversion [%] | Diol conversion [%] |
|---|---|---|---|
| 10.0 | 32 | 66.8 | 9.6 |
| 7.5 | 32 | 66.1 | 9.5 |
| 5.0 | 34 | 66.5 | 6.5 |
| 4.0 | 34 | 59.9 | 6.9 |
| 3.0 | 34 | 55.8 | 6.9 |
| 2.0 | 34 | 48.2 | 5.4 |
| 1.0 | 36 | 33.6 | 4.9 |
| 0.0 | — | — | — |

D) Preparation of Styrene Oxides Using Various Quantities of the Oxidizing Agent UHP Mini-emulsions were prepared, which contained the following components: 2.5 g styrene, 10 mole % decanoic acid, 5 wt. % lipase PS (all based on alkene); 12.5 ml water, 2.0 wt. % surfactant LUTENSOL AT50 (based on water); temperature 40° C.; pH value at start of reaction=4.2; and various quantities of the oxidizing agent UHP.

With a UHP quantity of 1.50 eq., a volume average drop diameter ($D_{50}$) of the disperse phase of 222 nm, measured by dynamic light scattering using a NICOMP 380 submicron particle sizer from PSS NICOMP, USA, was determined. The reaction conversion was determined as above.

| Quantity of UHP based on styrene [eq.] | Time (max. epoxide conversion) [h] | Epoxide conversion [%] | Diol conversion [%] |
|---|---|---|---|
| 2.50 | 20 | 55.0 | 3.5 |
| 2.00 | 28 | 60.8 | 6.7 |
| 1.75 | 28 | 64.3 | 6.8 |
| 1.50 | 34 | 66.5 | 6.5 |
| 1.25 | 32 | 65.4 | 12.2 |
| 1.10 | 30 | 62.1 | 14.1 |
| 0 | — | — | — |

E) Preparation of Styrene Oxides Using Different $C_{6-60}$ Carboxylic Acids Mini-emulsions were prepared, which contained the following components: 2.5 g styrene, 10 mole % of the $C_{6-60}$ carboxylic acid stated, 1.5 eq. UHP, 5 wt. % lipase PS (all based on alkene); 12.5 ml water, 2.0 wt. % surfactant LUTENSOL AT50 (based on water); temperature 40° C.; pH value at start of reaction=4.2

With the use of decanoic acid, a volume average drop diameter ($D_{50}$) of the disperse phase of 222 nm, measured by dynamic light scattering using a NICOMP 380 submicron particle sizer from PSS NICOMP, USA, was determined. The reaction conversion was determined as above.

| Carboxylic acid | Time (max. epoxide conversion) [h] | Epoxide conversion [%] | Diol conversion [%] |
|---|---|---|---|
| Hexanoic acid | 16 | 7.0 | 6.8 |
| Heptanoic acid | 20 | 25.8 | 10.6 |
| Octanoic acid | 26 | 42.6 | 7.7 |
| Nonanoic acid | 34 | 66.7 | 15.2 |
| Decanoic acid | 34 | 66.5 | 6.5 |
| Undecanoic acid | 42 | 62.1 | 10.0 |
| Dodecanoic acid | 42 | 59.7 | 8.6 |

With $C_{1-5}$ carboxylic acids, no significant reaction conversions were achieved.

E) Preparation of Styrene Oxides Using Different Quantities of Decanoic Acid Mini-emulsions were prepared, which contained the following components: 2.5 g styrene, stated quantity of decanoic acid, 1.5 eq. UHP, 5 wt. % lipase PS (all based on alkene); 12.5 ml water, 2.0 wt. % surfactant Lutensol AT50 (based on water); temperature 40° C.; pH value at start of reaction=4.2

With a decanoic acid content of 10 mole %, a volume average drop diameter ($D_{50}$) of the disperse phase of 222 nm,

| Quantity of decanoic acid based on styrene [mole %] | Time (max. epoxide conversion) [h] | Epoxide conversion [%] | Diol conversion [%] |
|---|---|---|---|
| 15.0 | 30 | 63.5 | 9.4 |
| 10.0 | 34 | 66.5 | 6.5 |
| 7.5 | 36 | 65.4 | 7.7 |
| 5.0 | 46 | 62.6 | 10.5 |
| 2.5 | 72 | 53.1 | 12.5 |
| 1.0 | 98 | 37.8 | 5.9 |
| 0 | — | — | — |

The invention claimed is:

1. A mini-emulsion for producing epoxides and percarboxylic acids comprising:
   (a) a lipase [EC 3.3.3.3];
   (b) a continuous phase containing water and an oxidizing agent; and
   (c) a dispersed phase containing a $C_{6-60}$ carboxylic acid wherein the continuous phase is substantially free of any organic solvents.

2. The mini-emulsion according to claim 1, wherein the dispersed phase is dispersed in the continuous phase as drops, and wherein the volume average drop diameter of the dispersed phase is 100 nm to 600 nm.

3. The mini-emulsion according to claim 1, wherein the lipase is a naturally existing lipase.

4. The mini-emulsion according to claim 3, wherein the naturally existing sources of the lipase is selected from the group consisting of *Thermomyces lanuginosus, Pseudomonas cepacia, Pseudomonas stutzeri, Rhizopus* sp., *Pseudomonas fluorescens, Penicillium camenbertii, Pseudomonas cepacia, Aspergillus niger, Achromobacter* sp., *Alcaligenes* sp., *Alcaligenes* sp, *Candida cylindracea, Candida cylindracea*, lipozyme TL IM, lipozyme TL 100L, *Candida antarctica* lipase B, *Candida antarctica* lipase A and *Candida rugosa* lipase.

5. The mini-emulsion according to claim 1, wherein the oxidizing agent is hydrogen peroxide and/or hydrogen peroxide-releasing reagents.

6. The mini-emulsion according to claim 1, wherein the oxidizing agent is an amine-hydrogen peroxide complex.

7. The mini-emulsion according to claim 1, wherein the $C_{6-60}$ carboxylic acid is selected from hexanoic acid, heptanoic acid, octanoic acid, nonanoic acid, decanoic acid, undecanoic acid or dodecanoic acid.

8. The mini-emulsion according to claim 1, wherein the mini-emulsion further comprising a surfactant or a hydrophobic substance.

9. The mini-emulsion according to claim 1, wherein the dispersed phase further comprises a reactant.

10. The mini-emulsion according to claim 9, wherein the reactant is an alkene and/or a cyclic ketone.

11. The mini-emulsion according to claim 9, wherein the molar ratio of the oxidizing agent to the reactant is 1.1:1 to 3:1.

12. The mini-emulsion according to claim 9, wherein the molar ratio of the $C_{6-60}$ carboxylic acid to the reactant is 10:1 to 1:10,000.

13. A mini-emulsion for producing epoxides and percarboxylic acids comprising:
   (a) 0.01 to 5 wt % of a lipase [EC 3.3.3.3];
   (b) a continuous phase containing water and an oxidizing agent; and
   (c) a dispersed phase containing a $C_{6-60}$ carboxylic acid wherein the continuous phase is substantially free of any organic solvents.

14. The mini-emulsion according to claim 13, wherein the lipase [EC 3.1.1.3] is selected from the group consisting of *Thermomyces lanuginosus, Pseudomonas cepacia, Pseudomonas stutzeri, Rhizopus* sp., *Pseudomonas fluorescens, Penicillium camenbertii, Pseudomonas cepacia, Aspergillus niger, Achromobacter* sp., *Alcaligenes* sp., *Alcaligenes* sp, *Candida cylindracea, Candida cylindracea*, lipozyme TL IM, lipozyme TL 100L, *Candida antarctica* lipase B, *Candida antarctica* lipase A and *Candida rugosa* lipase.

15. The mini-emulsion according to claim 13, wherein the oxidizing agent is hydrogen peroxide and/or hydrogen peroxide-releasing reagents.

16. The mini-emulsion according to claim 13, wherein the $C_{6-60}$ carboxylic acid is selected from hexanoic acid, heptanoic acid, octanoic acid, nonanoic acid, decanoic acid, undecanoic acid or dodecanoic acid.

17. The mini-emulsion according to claim 13, wherein the mini-emulsion further comprising a surfactant or a hydrophobic substance.

18. The mini-emulsion according to claim 13, wherein the dispersed phase further comprises a reactant, which is an alkene and/or a cyclic ketone.

* * * * *